United States Patent [19]

Aalto et al.

[11] Patent Number: 5,500,229
[45] Date of Patent: Mar. 19, 1996

[54] COLOSTRUM FRACTION, A PROCESS OF PREPARING IT AND ITS USE AS A SUPPLEMENT IN CELL CULTURE MEDIA

[75] Inventors: Jouni Aalto, Kirkkonummi; Raimo Pakkanen, Vantaa; Lea Satama, Helsinki; Jyrki Luopa, Espoo; Timo Allén, Vantaa; Arja Virtanen; Ari Kanttinen, both of Helsinki, all of Finland

[73] Assignee: Viable Bioproducts, Ltd., Finland

[21] Appl. No.: 166,911

[22] Filed: Dec. 15, 1993

Related U.S. Application Data

[63] Continuation of Ser. No. 792,818, Nov. 15, 1991, abandoned.

[30] Foreign Application Priority Data

Oct. 17, 1991 [FI] Finland .................................. 914911

[51] Int. Cl.⁶ .............................. A23C 9/12; C12N 5/00; C12N 1/00; C12N 1/18
[52] U.S. Cl. ..................... 424/535; 426/34; 435/240.2; 435/240.26; 435/240.3; 435/243; 435/256.8
[58] Field of Search ............................. 424/535; 435/240, 435/240.2, 240.26, 240.3, 243, 252.1, 256.8; 426/2, 34

[56] References Cited

U.S. PATENT DOCUMENTS

| | | | |
|---|---|---|---|
| 3,122,476 | 2/1964 | Gaeta | 167/74 |
| 4,051,235 | 9/1977 | Plymate | 424/85 |
| 4,402,938 | 9/1983 | Collins et al. | 424/85 |
| 4,440,860 | 4/1984 | Klagsbrun | 435/240 |
| 4,473,647 | 9/1984 | Carpenter et al. | 435/240 |
| 4,644,056 | 2/1987 | Kothe et al. | 530/387 |
| 4,834,974 | 5/1989 | Stott et al. | 424/85.8 |
| 4,866,037 | 9/1989 | Delepesse | 514/8 |

FOREIGN PATENT DOCUMENTS

| | | |
|---|---|---|
| 0219372 | 4/1987 | European Pat. Off. . |
| 0249932 | 12/1987 | European Pat. Off. . |
| 0307373 | 3/1989 | European Pat. Off. . |
| 0313515 | 4/1989 | European Pat. Off. . |
| 0391416 | 10/1990 | European Pat. Off. . |
| WO89/10064 | 11/1989 | WIPO . |
| WO90/06357 | 6/1990 | WIPO . |

OTHER PUBLICATIONS

PCT International Search Report, dated Jan. 20, 1993.
Biotechnology Techniques, (1988) vol. 2, No. 4, pp. 253–258, Damerdhjii et al.
Lait 70, (1990) pp. 313–324, Biochemical Aspects of a Whey Fraction etc., Derouiche et al.
Endocrinology, vol. 115 (1984) pp. 273–282, Human and Bovine Milk etc. Shing et al.
Methods of Enzymology, vol. 146, (1987), edited by Barnes et al.
Biochem. J. 251 (1988) pp. 95–103, Insulin–like Growth Factos etc. Francis et al.
O. Damerdji et al "Utiliz. of Whey Fractions as a Subst. for FSC in Culture Media" Biotech Tech. 1988 (2) pp. 253–258.
Shing et al., Purification of Polypeptide Growth Factors from Milk, 1987, 42–48.

Primary Examiner—Marian C. Knode
Assistant Examiner—Deborah K. Ware
Attorney, Agent, or Firm—Finnegan, Henderson, Farabow, Garrett & Dunner

[57] ABSTRACT

The invention discloses a colostrum fraction having a low endotoxin, protein and immunoglobulin concentration. The colostrum fraction is prepared by ultrafiltration of defatted colostrum pretreated in a desired manner by using a membrane having a molecular weight cut off of 100,000 daltons. The invention also discloses the use of the colostrum fraction as a supplement in cell culture media.

4 Claims, 3 Drawing Sheets

FIG. 6
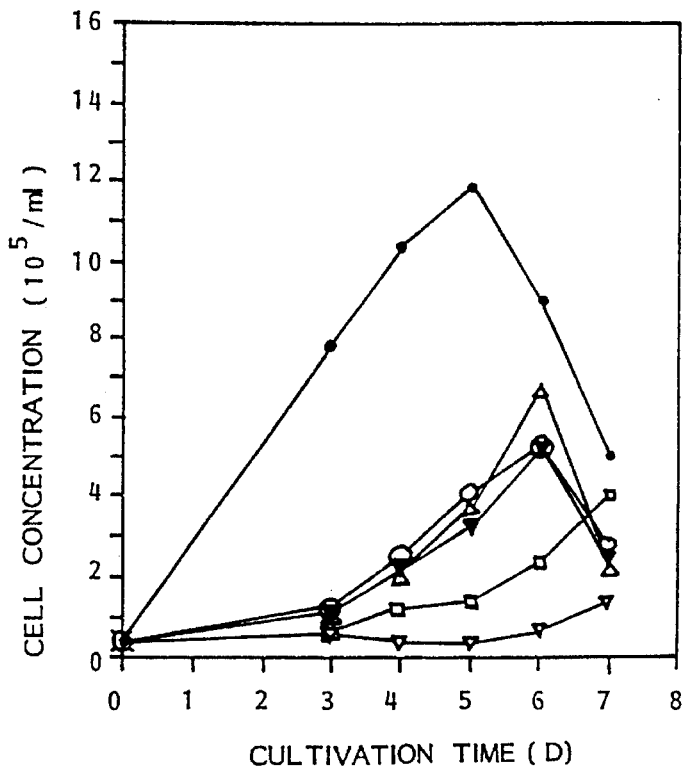
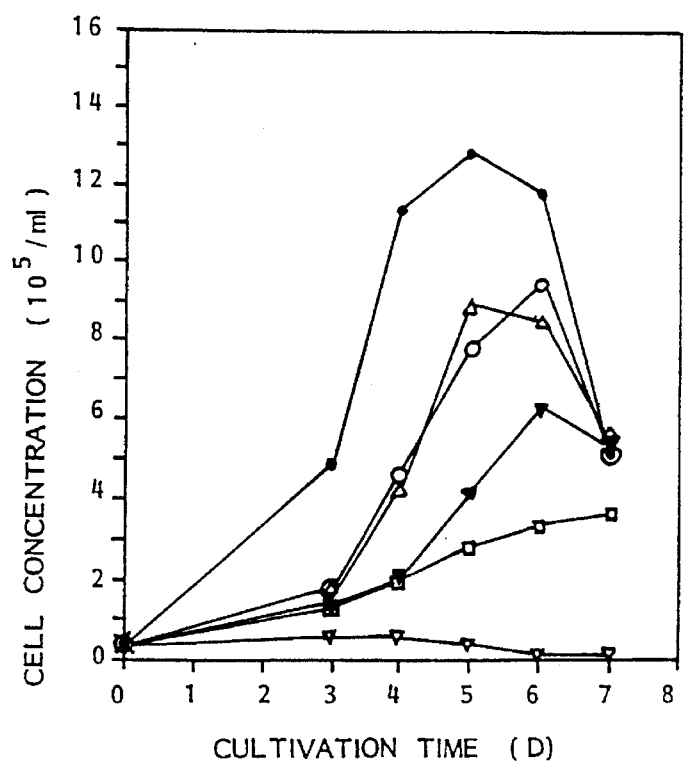
FIG. 5

5,500,229

COLOSTRUM FRACTION, A PROCESS OF PREPARING IT AND ITS USE AS A SUPPLEMENT IN CELL CULTURE MEDIA

This application is a continuation of application Ser. No. 07/792,818, filed Nov. 15, 1991, now abandoned.

FIELD OF THE INVENTION

The invention relates to a colostrum fraction, a process of preparing it, and its use as a supplement in cell culture media. The colostrum fraction according to the invention has a low endotoxin, protein and immunoglobulin concentration and it is prepared by ultrafiltration of pretreated colostrum.

BACKGROUND OF THE INVENTION

In the cultivation of mammal cells in vitro, the basal medium is traditionally supplemented with mammal blood serum, which contains several partly unknown cell growth promoting agents, such as growth factors, vitamins, trace elements, hormones, binding proteins and attachment factors. A serum suitable for most purposes is fetal bovine serum, the price of which has increased greatly with increasing demand in recent years. Another reason for the high price is the limited availability of sufficiently pure serum. Besides the high price, another problem with serum is its complex composition and especially the high protein concentration, which hampers the isolation of produced substances from the culture medium. There is also a high risk of contamination when using serum as a supplement in media. Both technologically and economically, monoclonal antibody production forms an important part of animal cell culture technology. Monoclonal antibodies are produced in large quantities for a variety of clinical and scientific purposes. In large-scale production of monoclonal antibodies, it is important to use a suitable culture medium. Antibody production should be continuous and reproducible; process costs should be as low as possible; antibodies should be readily purifiable; and contamination caused by microbes and endotoxins should be avoided. The same applies to the production of other biological substances, such as growth factors, hormones and vaccines, which are produced for clinical purposes by culturing genetically engineered animal cells. It is, however, very difficult to meet these requirements when using fetal bovine serum as a cell culture supplement.

Therefore, attempts have been made to find alternatives for the use of serum by developing various basal media and serum substitutes. They contain completely or partly purified growth promoting agents produced biosynthetically or isolated directly from a biological substance. Such growth promoting agents, e.g. various peptide growth factors such as insulin and insulin-like growth factors (IGF-1 and IGF-2), are not only present in serum but also in bovine colostrum. The synthesis, isolation and purification of growth factors are usually difficult to carry out, and literature does not teach any methods suitable for large-scale production. The use of purified growth factors is further limited by their high cost, which is even higher than that of fetal serum.

It is known from literature to use whey fractions obtained as a by-product in the production of milk and cheese as a supplement in cell culture media. However, the growth promoting activity of milk decreases sharply after calving, being very low, almost negligible, as soon as three days after calving as well as at subsequent lactation stages. On the other hand, milk possibly contains other cell growth promoting agents, nutrients, etc, which may promote the growth of cells.

It is also known that bovine colostrum and its fractions promote the growth of mammal cells in vitro. In addition to numerous components essential for cell growth, bovine colostrum, however, contains high amounts of immunoglobulins, mainly IgG, and other proteins, such as casein micelles, α-lactalbumin, β-lactoglobulin, and albumin. Immediately after lactation the IgG concentration may be as high as 40 to 60 g/l. This is a clear disadvantage when colostrum is used as such for the cultivation of hybridoma cultures, since it makes the isolation and purification of hybridoma products more difficult.

Another serious problem is associated with psychrotrophic microorganisms, mainly gram-negative bacteria, which are the most common spoilers of milk during storage. Lipopolysaccharides (endotoxins) produced by microorganisms are responsible for many pathophysiological effects accompanying infections caused by gram-negative bacteria. Thus endotoxins are extremely harmful contaminants, and their removal is essential especially when the substances produced in cell culture are intended for human use.

EP Patent Application 219 372, Linden et al., describes fractions of ordinary milk having a certain molecular weight, their preparation and use in cell culture media. This patent document teaches that milk is first ultracentrifuged, which is technically difficult to carry out in large-scale purification. Fractionation itself is then carried out by ultrafiltration based on the different molecular sizes of the substances and having a low resolution capacity. Accordingly, the protein concentration of the final product is very high in relation to the growth promoting activity. The inventors also describe the use of whey or whey fractions obtained as a by-product in the production of cheese in the cultivation of mammal cells (*Biotechnology Techniques* 2 (1988) p. 253–258, Damerdhjii et al., and Lait 70 (1990) p. 313–324, Derouiche et al.). The problem here is also the very high protein concentration and the risk of chemical and microbiological contamination.

EP Patent Application 313 515, Bürk, R. R. & Cox, D., describes a polypeptide growth factor in milk, processes for separating and purifying it from milk and milk products, and its use as a pharmaceutical, dietary additive, and cell culture media supplement. The process of this patent document comprises cation exchange chromatography, hydrophobic interaction chromatography, size exclusion chromatography, and polyacrylamide gel electrophoresis. As already mentioned above, the growth promoting activity of milk decreases sharply after calving. However, colostrum and its treatment are not referred to in this patent document.

U.S. Pat. No. 4,440,860, Klagsbrun, describes cell culture media containing milk or colostrum and fibronectin, and the preparation of such media. It is recited that the fractions are prepared by gel filtration and isoelectric focusing, which is not suitable for large-scale production. It is not disclosed in the patent document how the microbiological purity of the final product is ensured. Instead of comparing the growth promoting activity of the fractions described in the patent document with fetal bovine serum, the most common type of serum used in cell culture media, it is compared with calf serum having a substantially lower activity. The endotoxin concentration of the fractions is not mentioned at all. Furthermore, it is to be noted that it is assumed in the patent document that the growth factor fractions of the colostrum of different mammal species are similar. However, further research has shown that the principal growth factors of e.g. bovine and human colostrum deviate from each other to such an extent that they cannot be isolated by the same method (*Endocrinology* 115 (1984) p. 273–282, Shing, Y. W. & Klagsbrun, M.).

In *Methods in Enzymology*, vol. 146, edited by Barnes D. and Sirbasku, D. A., Shing et al. describe a process of purifying a bovine colostrum growth factor (BCGF) based on cation exchange, isoelectric focusing and high-resolution exclusion chromatography. The method is not suitable for growth factor isolation on industrial scale.

Francis et al. have isolated and characterized insulin-like growth factors IGF-1 and IGF-2 from bovine colostrum by a process described in *Biochem. J.* 251 (1988) p. 95–103. These growth factors have a molecular weight of 8,000 and 7,000 D, respectively, and they are nearly identical in structure with the corresponding human growth factors. This complicated process comprises many steps, such as several cation exchange chromatography and reversed-phase HPLC steps, and so it is not suitable for large-scale production.

The known methods thus all comprise many steps and are difficult to carry out and unsuitable for large-scale production. Complicated and time-consuming purification operations also increase the product cost. It is also to be noted that it is not disclosed in the cited documents how the microbiological purity of the final product is ensured. Neither do they mention the endotoxin concentration of the final product. Endotoxins and problems caused by them are not described in the cited documents, so they do not either suggest any solution to these problems.

The major drawbacks of colostrum when used as such as culture media supplement are its high protein and IgG concentration and usually the high endotoxin concentration. Viruses present in colostrum may also inhibit cell growth or even kill cells. The high protein concentration of colostrum and the insoluble sediments contained in it also hamper the treatment of colostrum and make it difficult if not impossible to sterilize e.g. defatted colostrum through microfilters. If high amounts of defatted colostrum are added to a culture medium, precipitations will occur in the medium.

SUMMARY OF THE INVENTION

The object of the present invention is to overcome said difficulties and provide a colostrum fraction with growth promoting activity, said fraction having a low protein, endotoxin and immunoglobulin concentration.

Another object of the present invention is to provide a process for preparing said colostrum fraction. The process of the invention utilizes ultrafiltration of pretreated colostrum, and is also suitable for large-scale production.

The invention also provides for the use of said colostrum fraction as a supplement in cell culture media, and for cell culture media containing said colostrum fraction.

SHORT DESCRIPTION OF THE DRAWINGS

FIG. 1 shows the number of viable LPC1 cells as a function of time during continuous cultivation in a medium supplemented with ultrafiltrate FIG. 1A, whey FIG. 1B and defatted colostrum FIG. 1C. Initial supplement concentrations: 1% (●), 5% (▼), 10% (■), 15% (▲) and 20% (X). Whey and colostrum were filtrated consecutively through 0.8 and 0.2 μm filters before use.

Figure 1A:
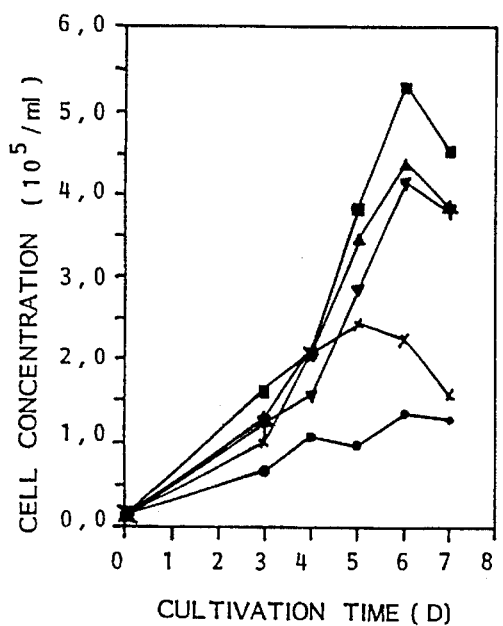

FIG. 5 shows the effect of sodium selenite on cell growth. LPC1 cells were cultured in 10% ultrafiltrate supplemented with 0.4 μM (o), 2 μM Δ, 6 μM (□) and 20 μM (▽) sodium selenite. (●) and (▼) represent LPC1 cells cultured in 10% FBS and 10% ultrafiltrate without sodium selenite, respectively.

FIG. 6 shows the effect of β-mercaptoethanol on cell growth. LPC1 cells were cultured in 10% ultrafiltrate supplemented with 5 μM (o), 15 μM (Δ), 50 μM (□) and 100 μM (▽) β-mercaptoethanol. (●) and (▼) represent LPC1 cells cultured in 10% FBS and 10% ultrafiltrate without β-mercaptoethanol, respectively.

DETAILED DESCRIPTION OF THE INVENTION

It has now been unexpectedly found out that a fraction having a very low protein and immunoglobulin concentration and a negligible endotoxin concentration can be prepared from bovine colostrum by a process described in this patent application. The final product contains all growth factors, trace elements, vitamins and other small-molecular compounds essential for cell proliferation present in colostrum. On the contrary, harmful endotoxins contained in milk are eliminated during the process. Possible virus particles are probably also eliminated, which naturally decreases the contamination risk of the final products of the cell culture.

The invention thus relates to a colostrum fraction having a low endotoxin, protein and immunoglobulin concentration.

The colostrum fraction according to the invention can be prepared by a process according to the invention, which process comprises subjecting pretreated colostrum to ultrafiltration by using a membrane having a cut off of 100,000, and recovering the filtrate.

The process according to the invention is thus based on ultrafiltration. Colostrum is pretreated to remove fat and possible cellular debris. If desired, a whey solution can be formed of defatted colostrum by removing casein e.g. by acid or enzyme precipitation. The obtained defatted colostrum or whey is then ultrafiltrated by utilizing a membrane having a cut off of 100,000, and the filtrate is recovered. As compared with the processes known from the prior art, the present process is extremely suitable for large-scale production, and the purity of the final product can be ensured e.g. by sterile filtration.

The process alternative in which no casein precipitation is carried out is more advantageous, as it is simpler and can be carried out at lower cost. On the other hand, if casein precipitation is carried out, a slightly better product is obtained, that is, the obtained ultrafiltrate has a lower protein and immunoglobulin concentration.

The colostrum fraction according to the invention is extremely useful as such or when complemented by other supplements for replacing partially or completely fetal bovine serum in widely used cell culture media. The effect of the fraction can be improved by adding one or more supplements, such as sodium selenite, insulin, ethanolamine, β-mercaptoethanol, bovine serum albumin, etc.

The colostrum fraction according to the invention is prepared from bovine colostrum. Preferably, the raw material is colostrum milked within a couple of days after calving. Colostrum can be frozen on the farm before being processed.

Fat and possible cellular debris are first removed from the colostrum e.g. by centrifugation, by means of a conventional dairy separator or by filtration.

If desired, defatted colostrum is subjected to a sterile filtration treatment, which comprises the filtration of the colostrum through one or several microfilters of different sizes. Sterile filtration is not necessary, but it speeds up the ultra-filtration and reduces the bacteria content of the fraction.

If desired, defatted colostrum can be processed further. For example, casein can be removed by acid precipitation by decreasing the pH of the mixture. The precipitation is carried out by e.g. hydrogen chloride or acetic acid, and the pH is decreased to about 4.5. The precipitation can be carried out at elevated temperature to reduce microbiological contaminants. The precipitation can also be carried out by enzymes. The precipitate can be separated from the mixture by various methods, such as by centrifugation or by tangential membrane filtration. After the separation of the precipitate, the mixture is neutralized and the obtained precipitate is removed. In this way, colostrum whey is obtained.

If desired, the obtained light yellow colostrum whey is subjected to sterile filtration as described above.

The obtained product is then ultrafiltrated by using a membrane having a nominal molecular weight limit of 100,000, and the filtrate passed through the membrane is recovered.

If desired, the ultrafiltrate fraction can be concentrated, sterile filtrated and/or lyophilized. The fraction can also be further purified, if desired.

For use, the colostrum fraction according to the invention is added to a culture medium. The optimum concentration of the fraction is about 5 to 15%, although smaller amounts can also be used. At very high concentrations, the fraction has an inhibitory effect on cell growth. If desired, the fraction is supplemented with additives or growth promoting agents. The agents to be used and their concentrations vary with the cell type. For example, when LPC1 hybridoma cells are grown in a 10% colostrum fraction supplemented with sodium selenite, the optimum concentration of sodium selenite is about 0.4 to 2 µM, whereas the optimum concentration for 3T3 cells is about 0.4 to 100 nM. Even though the cell inoculations are made at low cell concentrations (e.g. 15,000 cells/ml), the hybridomas can be added to the cell culture medium without any adaptation step.

As compared with fetal bovine serum, a lower maximum cell concentration is obtained in a culture medium supplemented with the colostrum fraction according to the invention. Economically, however, the fraction competes well with fetal serum. Better results can be obtained by optimizing the growing conditions. Due to the low protein concentration of the fraction, proteins produced by the cultured cells, such as monoclonal antibodies, are more readily purifiable than those obtained in a culture medium supplemented with serum. Purification of therapeutical proteins is further facilitated by the low endotoxin concentration of the ultrafiltrate. Low protein and endotoxin concentrations help to ensure that the produced proteins can also be administered to humans without any health risks.

The invention will be illustrated by the following examples, which are not intended to restrict the invention. In all the described cell cultures utilizing ultrafiltrates, transferrin was present (5 mg/ml).

Example 1

Preparation of a fraction from bovine colostrum

Bovine colostrum was collected from 16 different cows from five different farms. A 1-liter sample of colostrum was collected from each one of the first five milkings of each cow after the onset of lactation and frozen immediately. A batch of 80 liters was made by mixing an equal amount of colostrum from each one of the five milkings. The colostrum pool was divided into 1-liter aliquots and stored at −20° C. for further processing.

Colostrum was thawed and centrifuged at 10,000 g for 60 min. The top layer containing fat and the bottom layer containing cellular debris and other insoluble material were discarded. Casein was precipitated at 56° C. by adjusting pH to 4.6 by addition of 2 M HCl. The mixture was stirred for one hour, and then the precipitate was removed by centrifugation at 4° C. and 10,000 g for 60 min. Whey was incubated at 4° C. overnight, and pH was then adjusted to 7.0 by 4 M of NaOH. The precipitate was removed by centrifugation at room temperature as described above. The cleared whey was filtrated consecutively through 0.8 µm and 0.22 µm filters (Millipore Corporation, Bedford, Mass., USA), and the filtrate was further ultrafiltrated in a Minitan apparatus (Millipore) using polysulfone ultrafiltration plates having a nominal molecular weight limit of 100,000. The ultrafiltrate was filtrated through a 0.22 µm filter and stored at −20° C.

Example 2

Preparation of a fraction from bovine colostrum, an alternative approach

A colostrum fraction prepared as described in Example 1 was thawed and fat, cellular debris and other insoluble material were separated in a separator. The obtained defatted colostrum fraction was filtrated consecutively through 0.8 µm and 0.22 µm filters (Millipore Corporation, Bedford, Mass., USA), and the filtrate was ultrafiltrated in a Minitan apparatus (Millipore) by using polysulfone ultrafiltration plates having a nominal molecular weight limit of 100,000. The ultrafiltrate was filtrated through a 0.22 µm filter and stored at −20° C.

Example 3

Characterization of the fraction and intermediates

The protein concentration of the final products and intermediates obtained in Examples 1 and 2 was determined colorimetrically by a method described in Anal. Biochem. 72 (1976), p. 248–254, with bovine immunoglobulin as a standard. The monoclonal antibody concentration was determined by FPLC (Pharmacia, Uppsala, Sweden) by using a ProAna™Mabs protein G column (Perstorp Biolytica, Lund, Sweden) and with purified mouse IgG-1 as a standard, as described in J. Immunol. Meth. 114 (1988) p. 175–180. The total protein concentration and IgG concentration of the obtained products are shown in the following Table 1.

TABLE 1

Protein and IgG concentration of bovine colostrum, whey and ultrafiltrate

| Sample | IgG [g/l] | Total protein [g/l] |
|---|---|---|
| Defatted colostrum | 22.5 ± 1.0 | 67.1 ± 7.5 |
| Whey | 12.8 ± 1.1 | 19.6 ± 0.35 |
| Ultrafiltrate (Example 1) | 0.24 ± 0.01 | 1.15 ± 0.027 |
| Ultrafiltrate (Example 2) | 0.830 ± 0.341 | 3.48 ± 0.88 |

Endotoxins were determined by the Limulus Amebocyte Lysate (LAL) gel-clot method described in *Bull. John Hopkins Hospital* 115 (1964) p. 265–274, and the test kit was from Whittaker Bioproducts Inc. (Walkersville, Md., USA). The endotoxin standard was from the *E. coli* strain 055:B5. The concentration of the control standard endotoxin (CSE) was 10 EU/ng, and the sensitivity of the lysate was 0.06 EU/ml. The analyses were carried out according to the manufacturer's instructions. The water used for dilutions was pyrogen-free (Leiras Oy, Turku, Finland), and the dilutions were performed aseptically. The level of endotoxin was calculated by multiplying the reciprocal of the highest dilution of the test solution giving a positive endpoint by the lysate sensitivity. A positive control of a known concentration of endotoxin and a negative control of pyrogen-free water were used in every test. The endotoxin concentration of the products is shown in Table 2.

TABLE 2

Endotoxin concentration of bovine colostrum, whey and ultrafiltrate

| Sample | Endotoxin concentration [EU/ml] |
|---|---|
| Defatted colostrum | 7.7 ± 5.5 |
| Whey | 0.66 ± 0.36 |
| Ultrafiltrate (Example 1) | <0.24 |
| Ultrafiltrate (Example 2) | <4.6 |

The ultrafiltrate prepared as described in Example 1 contained less than 0.24 EU/ml of endotoxins. The product prepared in Example 2 showed a higher endotoxin concentration, which, however, was not more than that of products prepared with serum. Both ultrafiltrate and colostrum contained some inhibitors of the LAL test, but their effect could be overcome by diluting the samples (1:2) and heating them at 100° C. for about 2 min.

Example 4

Use of the fraction in the cultivation of hybridoma cells

Preparation of hybridomas

Balb/c mice were immunized intraperitoneally every third week either with 200 µg of lactoferrin (Sigma Chemical Co., St. Louis, Mo., USA) or with 200 µg of lactoperoxidase (Sigma). The first boost and the following two boosts were given in Freund's complete and incomplete adjuvant, respectively. The final boost was given in phosphate-buffered saline (PBS). The spleen of each animal was collected for fusion three days after the final boost. The spleen lymphocytes were fused with X63.Ag8.653 mouse myeloma cells as described in *Methods Enzymol* 73 (1975), p. 3–46, and the hybrids producing anti-lactoferrin and anti-lactoperoxidase antibodies were screened by the enzyme linked immunosorbent assay (ELISA) as described in *Laboratory Techniques in Biochemistry and Molecular Biology*, ed. by Burdon R. H. and Knippenberg P. H., Elsevier Science Publishers, Amsterdam, Holland. Subclasses of the antibodies were determined using commercial kits (Mouse-Typer Sub-Isotyping Kit, Bio-Rad, Richmond, Calif., USA, and Serotec Ltd., Oxford, UK) according to the manufacturer's instructions. Clones LFC6 and LFC1 produced anti-lactoferrin antibodies of the subclass IgG-1, and LPC1 produced anti-lactoperoxidase antibodies of the same subclass.

Cultivation of hybridomas

Cells were grown in a DMEM medium (Dulbecco's Modified Eagles Essential Medium, Flow Laboratories Ltd., Scotland, UK) supplemented with 4 mM of glutamine, 100 U/ml of penicillin, and 100 µg/ml of streptomycin (basal medium). Stock cultures were maintained in 75 $cm^2$ plastic flasks (Costar, Cambridge, Mass., USA) supplemented with 7% of fetal bovine serum (Flow). For subculture, cells growing in the exponential phase were centrifuged at 400 g for 5 min. The supernatant was discarded, and the cells were washed once with PBS. The cells were then suspended in a medium containing known amounts (0 to 20%) of fetal bovine serum, defatted bovine colostrum, whey or ultrafiltrate supplemented with human transferrin, 5 mg/l (Sigma). The cells in the test media were plated into 6-well microtiter plates (Costar) at a concentration of 15,000 cells/ml and incubated without medium change for 1 to 12 days. Cell counts were carried out in duplicate in a hemacytometer using trypan blue exclusion to determine cell viability.

Figure 1B:
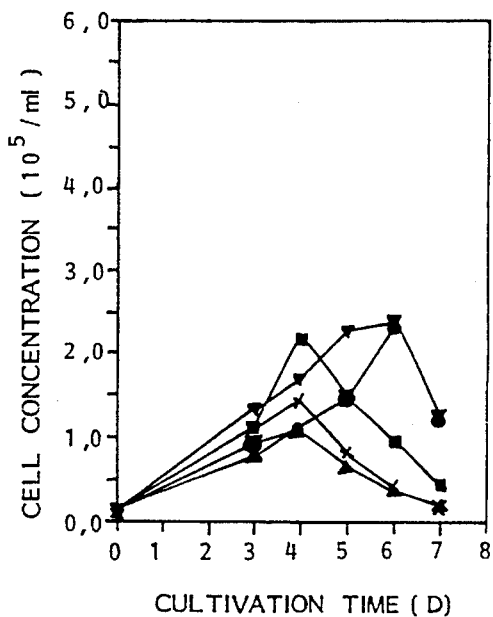
Figure 1C:
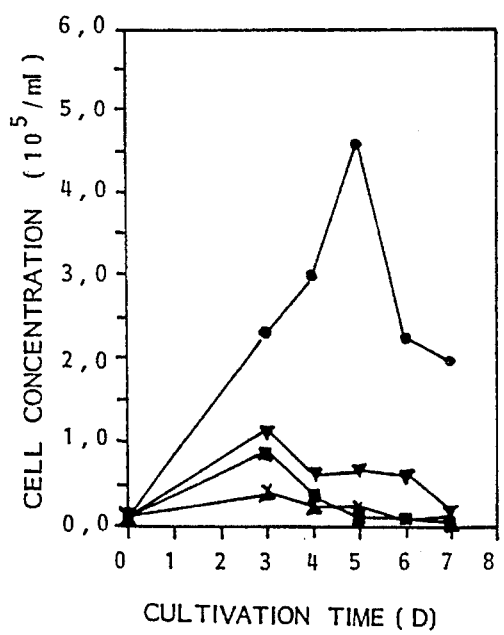

The results are shown graphically in FIG. 1, which shows the number of viable LPC1 cells as a function of time during continuous cultivation in a medium supplemented with ultrafiltrate (A), whey (B) and defatted colostrum (C). The following amounts of supplement prepared as described in Example 1 were added to the medium: 1% (●), 5% (▼), 10% (■), 15% (▲) and 20% (X). The highest cell concentration $5.31 \times 10^5$/ml was obtained when 10% ultrafiltrate was used (FIG. 1A). With defatted colostrum, the highest cell count $4.61 \times 10^5$/ml was obtained when 1% colostrum was used (FIG. 1C). The cell concentration remained low at all whey concentrations (FIG. 1B).

Figure 2:
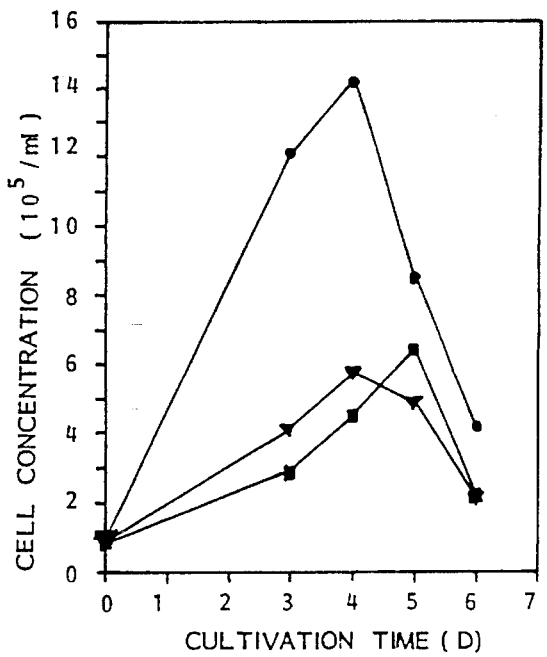
FIG. 2 shows the number of viable LPC1 cells as a function of time during continuous cultivation in 10% FBS (●), 10% ultrafiltrate prepared as described in Example 1 (■), and 10% ultrafiltrate prepared as described in Example 2 (▼).

In FIG. 2, the growth of LPC1 cells is compared in 10% fetal bovine serum (●), in 10% ultra-filtrate (■) prepared as described in Example 1, and in 10% ultrafiltrate (▼) prepared as described in Example 2.

Figure 3:
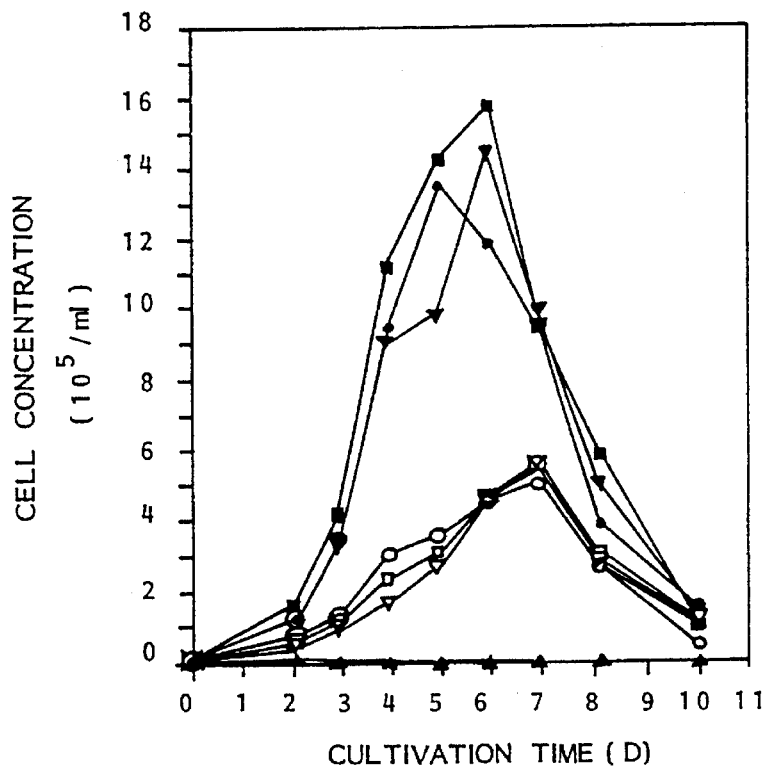
FIG. 3 shows the growth curves of LFC1, LFC6 and LPC1 hybridomas grown in media supplemented as follows: LPC1 in 10% FBS (●), 10% ultrafiltrate (o) or in basal medium with 5 mg/l transferrin alone (▲); LFC1 in 10% FBS (▼) or 10% ultrafiltrate (▽) and LFC6 cultured in 10% FBS (■) or 10% ultrafiltrate (□).

The growth curves of LFC1, LFC6 and LPC1 hybridomas grown in media supplemented in different ways are shown in FIG. 3. The hybridoma LPC1 was grown in 10% fetal bovine serum (●), 10% ultrafiltrate (o) and in a basal medium supplemented solely with 5 mg/ml of transferrin (▲); the hybridoma LFC1 was grown in 10% fetal bovine serum (▼) and 10% ultrafiltrate (∇), and the hybridoma LFC6 was grown in 10% fetal bovine serum (■) and 10% ultrafiltrate (□).

No changes could be observed in the growth characteristics of the cell lines. The highest hybridoma cell concentrations were $13.6–15.8 \times 10^5$/ml in 10% fetal bovine serum and 5.12–5.64×10$^5$/ml in 10% ultrafiltrate. The maximum cell concentration obtained by the ultrafiltrate was thus about 35 to 40% of that obtained by fetal serum. The doubling time of the hybridomas was about 17 hours and about 35 hours in fetal serum and ultrafiltrate, respectively. If the basal medium was supplemented with transferrin only, the hybridoma growth was negligible. On the other hand, the ultrafiltrate was not able to promote hybridoma proliferation in the absence of transferrin.

Production of monoclonal antibodies

Figure 4:
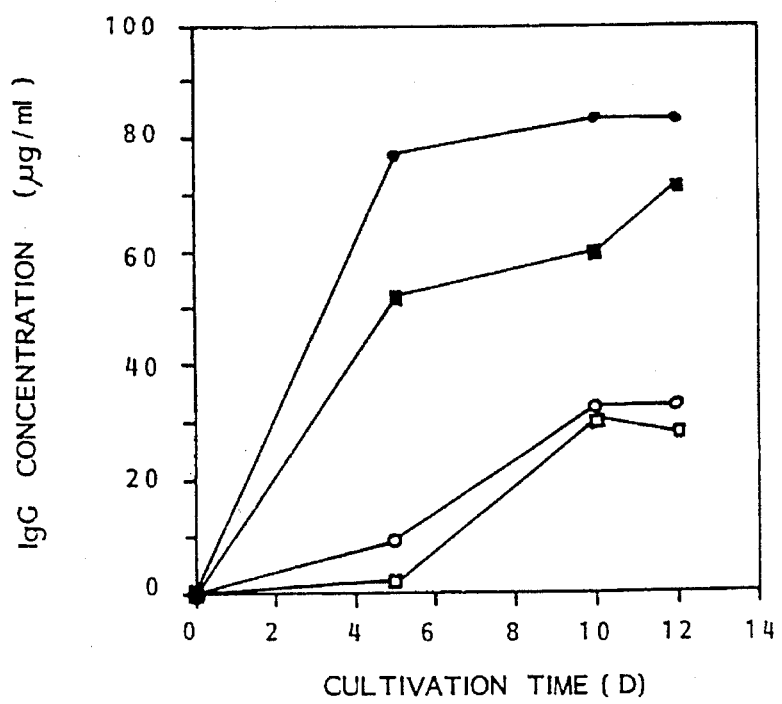
FIG. 4 shows the concentration of IgG produced by LFC1 cultured in 10% FBS (●) or 10% ultrafiltrate (o) and LFC6 cultured in 10% FBS (■) or 10% ultrafiltrate (□).

FIG. 4 shows the antibody production of LFC1 and LFC6 hybridoma cells in a medium containing 10% of fetal bovine serum (FBS) and 10% of ultrafiltrate (UF), respectively [LFC1: FBS (●), UF (o); LFC6: FBS (■), UF (□)]. After continuous cultivation for 12 days the antibody concentrations in 10% ultrafiltrate were 40% (LFC1) and 42% (LFC6) of that obtained when using 10% fetal serum (83.5 mg/l for LPC1 and 72.0 mg/l for LPC6).

Example 5

Use of fractions in the cultivation of other cells

The effect of the fraction prepared as described in Example 1 on the growth of other cells was examined by using three different cell types. Vero (kidney cell line of the African Green Monkey, *Cercopithecus aethiops*, ATCC CCL 81), CHO-Ki (ovary cell line of the Chinese hamster, *Cricetulus griseus*, ATCC CCL 61) and 3T3 (mouse embryo fibroblast cell line, ATCC CCL 92) cells were grown in a basal medium containing varying amounts of ultrafiltrate. Stock cultures were stored in 10% fetal bovine serum. To obtain subcultures, the cells were washed once with PBS and suspended in a basal medium supplemented with varying amounts (0 to 20%) of ultrafiltrate and 5 mg/ml of transferrin. The cells in the test media were plated into 24-well microtiter plates (Costar) at a concentration of 20,000 viable cells/ml and incubated without medium changes for 7 days. The cell counts were carried out in duplicate in a hemacytometer by trypan blue exclusion. The results are shown in Table 3.

TABLE 3

Effect of ultrafiltrate on the growth of different cell types

| Ultrafiltrate concentration | Cells/ml | | |
|---|---|---|---|
| | Vero | CHO-Ki | 3T3 |
| 20% | 26,000 | 13,000 | 46,000 |
| 15% | 116,000 | 17,000 | 108,000 |
| 10% | 133,000 | 16,000 | 81,000 |
| 5% | 51,000 | 7,800 | 47,000 |
| 1% | 11,000 | 0 | 7,800 |
| 0% | 19,000 | 5,600 | 2,200 |

It appears from the results that the ultrafiltrate promotes the growth of all cell lines, though the different cell types react in different ways. An ultrafiltrate concentration as low as 1% is already effective, and the concentrations between 5 and 15% are regarded as advantageous, concentrations between 10 and 15% being particularly advantageous.

Example 6

Fraction supplementation

The ultrafiltrate product according to the invention always contains transferrin. In addition, its growth promoting properties can be improved with various supplements. The effect of sodium selenite and β-mercaptoethanol additions on the growth of 3T3 cells was determined in the following way. The cells were washed once with PBS and suspended in a basal medium supplemented with 15% of ultrafiltrate, 5 mg/ml of transferrin and varying amounts of sodium selenite or β-mercaptoethanol. The cultivation and counting of the cells were carried out as described in Examples 4 and 5. The results are shown in Table 4.

TABLE 4

Effect of ultrafiltrate supplemented with sodium selenite and β-mercaptoethanol on cell growth

| β-MeOH [µM] | Cells/ml | Na-selenite [nM] | Cells/ml |
|---|---|---|---|
| 0 | 69,000 | 0 | 69,000 |
| 0.5 | 61,000 | 0.4 | 111,000 |
| 1.0 | 159,000 | 4.0 | 128,000 |
| 5.0 | 147,000 | 40 | 109,000 |
| 10 | 130,000 | 100 | 136,000 |
| 20 | 90,000 | 300 | 74,000 |

FIGS. 5 and 6 illustrate the favorable effect of sodium selenite and β-mercaptoethanol, respectively, on the growth of LPC1 hybridoma cells. The cells were grown in 10% ultrafiltrate supplemented with 0.4 µM (o), 2 µM (Δ), 6 µM (□) and 20 µM (∇) of sodium selenite (FIG. 5) and 5 µM (o), 15 µM (Δ), 50 µM (□) and 100 µM (∇) of β-mercaptoethanol (FIG. 6). (●) and (▼) represent LPC1 cells grown in 10% fetal bovine serum and 10% ultrafiltrate, respectively, without adding the above-mentioned compounds.

It appears from the results that the effect of the supplements and the useful concentration ranges vary with the cell type. For example, sodium selenite has a promoting effect even in very small amounts (nanomole level) whereas the effect of β-mercaptoethanol is obtained only on the micromole level.

We claim:

1. A colostrum fraction having a low endotoxin, protein and immunoglobulin concentration suitable for use in cell culture media, said colostrum fraction is prepared by:

(a) removing fat from colostrum to obtain a defatted colostrum;

(b) filtrating the defatted colostrum sequentially through 0.8 µm and 0.22 µm filters; and (c) filtering by one-step ultrafiltration using membrane having a molecular weight cut off of 100,000 daltons, and recovering a filtrate to obtain the colostrum fraction.

2. The colostrum fraction of claim 1, wherein casein is removed therefrom by precipitation.

3. A cell culture medium for eukaryotic cells comprising transferrin and the colostrum fraction in claim 1.

4. The cell culture medium of claim 3, further comprising one or more additional supplements selected from the group consisting of sodium selenite and β-mercaptoethanol.

\* \* \* \* \*

UNITED STATES PATENT AND TRADEMARK OFFICE
CERTIFICATE OF CORRECTION

PATENT NO. : 5,500,229

DATED : March 19, 1996

INVENTOR(S) : Jouni Aalto et al.

It is certified that error appears in the above-indentified patent and that said Letters Patent is hereby corrected as shown below:

Claim 1, column 10, line 51, after "using" insert --a--.

Signed and Sealed this

Fourth Day of June, 1996

BRUCE LEHMAN

*Attest:*

*Attesting Officer*  *Commissioner of Patents and Trademarks*